United States Patent [19]  [11] 4,398,092
Carlson  [45] Aug. 9, 1983

[54] SHAPED DETECTOR

[75] Inventor: Roland W. Carlson, Lyndhurst, Ohio

[73] Assignee: Technicare Corporation, Solon, Ohio

[21] Appl. No.: 265,714

[22] Filed: May 20, 1981

Related U.S. Application Data

[63] Continuation-in-part of Ser. No. 64,835, Aug. 8, 1979, Pat. No. 4,292,538.

[51] Int. Cl.³ .............................................. G01T 1/20
[52] U.S. Cl. ............................ 250/361 R; 250/363 R
[58] Field of Search .............. 250/361 R, 363 R, 366, 250/367, 369; 378/19

[56] References Cited

U.S. PATENT DOCUMENTS

| | | | |
|---|---|---|---|
| 3,399,302 | 8/1968 | Carrell | 250/367 X |
| 4,037,105 | 7/1977 | Laurer | 250/367 |
| 4,070,581 | 1/1978 | Gibbons et al. | 250/366 X |
| 4,180,737 | 12/1979 | Kingsley | 250/367 |

Primary Examiner—Davis L. Willis
Attorney, Agent, or Firm—Michael A. Kaufman

[57] ABSTRACT

A radiation detector or detector array which has a non-constant spatial response individually and in combination with a tomographic scanner. The detector has a first dimension which is oriented parallel to the plane of the scan circle in the scanner. Along the first dimension, the detector is most responsive to radiation received along a centered segment of the dimension and less responsive to radiation received along edge segments. This non-constant spatial response can be achieved in a detector comprised of a scintillation crystal and a photoelectric transducer. The scintillation crystal in one embodiment is composed of three crystals arranged in layers, with the center crystal having the greatest light conversion efficiency. In a preferred embodiment, the non-constant spatial response is achieved in a detector comprised of a single scintillation crystal whose response is shaped by inducing along said first dimension a scintillation conversion efficiency gradient. In the single crystal embodiment, the gradient is chosen so that the crystal has greater conversion efficiency centrally than peripherally.

9 Claims, 19 Drawing Figures

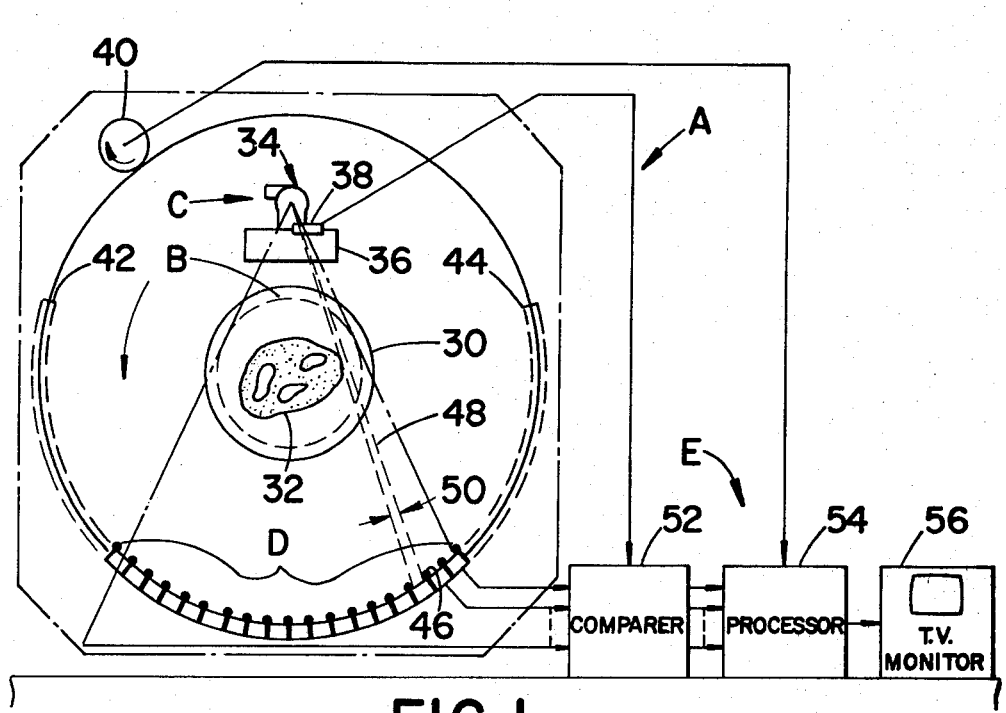
FIG.1
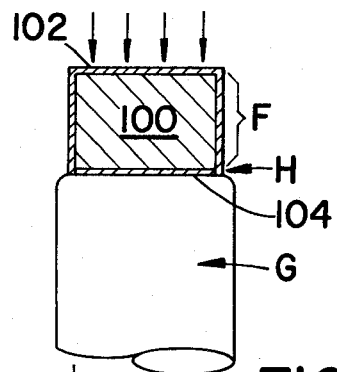
FIG.2A
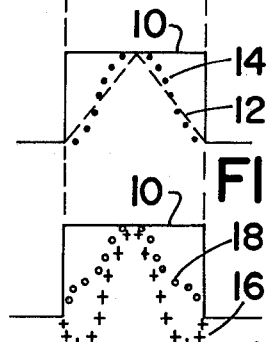
FIG.2B
FIG.2C
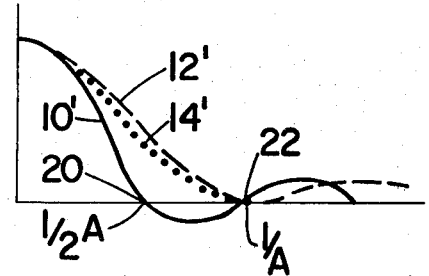
FIG.3
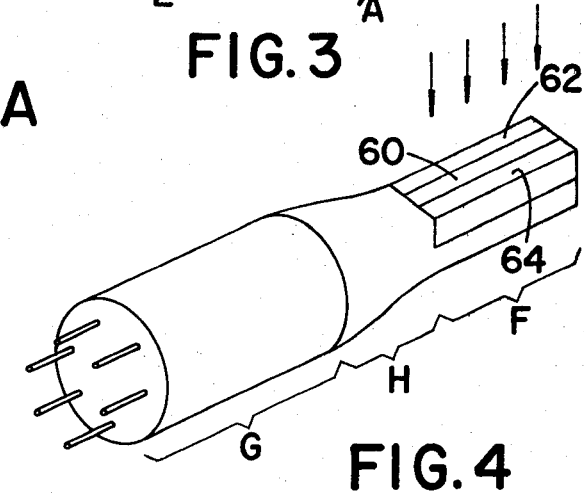
FIG.4

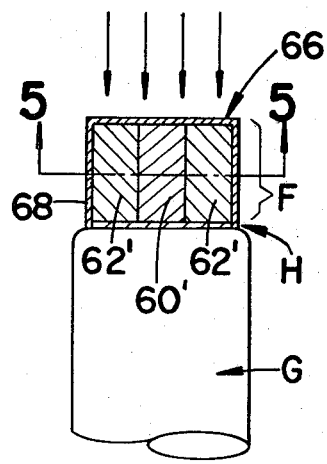
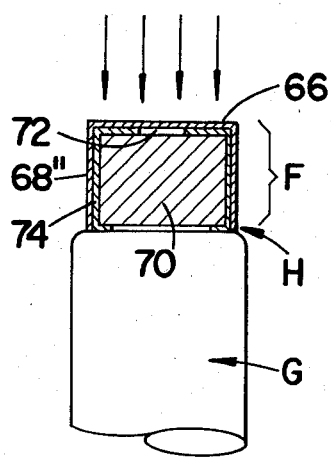
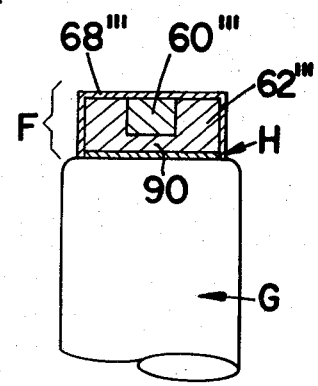
FIG.5A     FIG.6     FIG.8
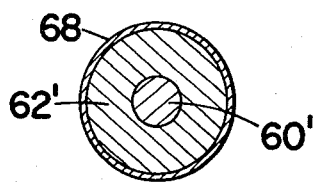
FIG.5B
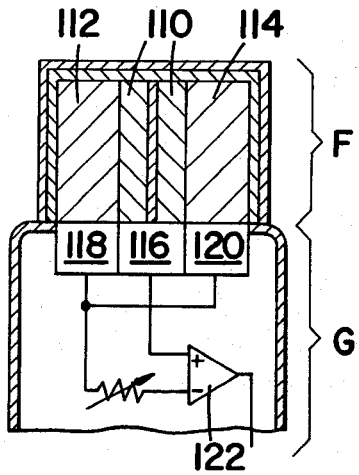
FIG.9
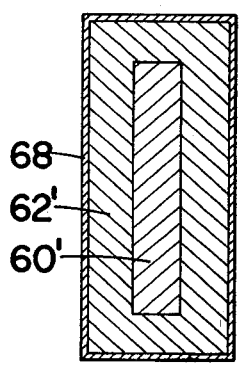
FIG.5C
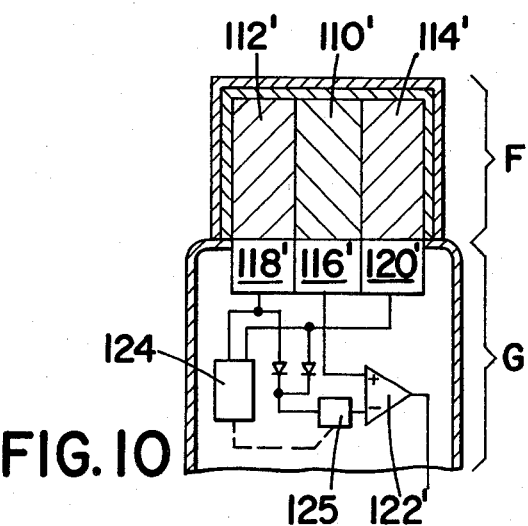
FIG.10

SHAPED DETECTOR

CROSS-REFERENCE TO RELATED APPLICATION

This application is a continuation-in-part of application Ser. No. 064,835, filed Aug. 8, 1979 now U.S. Pat. No. 4,292,538.

BACKGROUND OF THE INVENTION

This application pertains to the art of radiant energy detection and more particularly, to apparatus for converting variations in incident, gamma or x-radiation into corresponding variations in an electrical property, such as changes in output voltage, current or resistance. The invention is particularly applicable to computerized axial tomographic scanners and will be described with particular reference thereto. It will be appreciated, however, that the invention has broader applications such as industrial flaw detectors and other apparatus which detect radiation with high resolution.

Generally, a computerized axial tomographic scanner comprises a source of radiation for irradiating a patient and a plurality of radiation detectors positioned opposite the patient from the radiation source. The detectors receive radiation beams which have passed through the patient along known paths. At least the radiation source is movably mounted for irradiating the patient from a plurality of directions. The detectors are positioned to detect the radiation beams along a plurality of interesecting paths through a planar slice of the patient. With well-known computer reconstruction techniques, the variation or attenuation of the radiation beams along the plurality of interesecting paths is reconstructed into an image of the planar region of the patient. The thickness of the beams along an axis generally transverse to the planar slice affects the thickness of the planar slice examined. The width of the beams affects the resolution of the reconstructed image. The width is an axis within the plane which is generally transverse to the thickness axis and transverse to the path between the source and the detector. The radiation detectors generally consist of a scintillation crystal positioned to receive radiation and a photomultiplier tube optically coupled to the scintillation crystal. Alternately, the detectors may consist of a scintillation crystal optically coupled with a photodiode, a solid state radiation detector or an ionizable gas detector.

Generally, medical diagnosticians achieve the preferred results from tomographic scanners which have high resolution and low noise. A major factor in determining the resolution is the width of the radiation beams. The width may be determined by the width of the radiation receptive surface of the detector or by a source collimator. A scintillation crystal-photomultiplier tube detector generally has the scintillation crystal mounted in a support behind an aperture. The width of the aperture limits the width of the beam for reconstruction purposes. Additional radiation outside the beam which does not impinge on the receptive surface of the detector does not contribute to the reconstructed image even though it may pass through the patient.

Noise degrades the tomographic image. Generally, the amount of noise is related to the inverse square root of the number of photons of radiation received by the detector. Increasing the radiation receptive surface of the detector decreases the noise.

Accordingly, there is usually a trade-off between noise and resolution. Increasing the width of the radiation receptive surface of the detector reduces noise but also reduces resolution. Decreasing the width of the detector increases resolution but also increases noise.

The present invention contemplates a new and improved radiation detection apparatus which overcomes the above problems and others. The present invention contemplates a radiation detector which improves resolution without a corresponding increase in noise. Alternately, the present invention provides a detector that reduces noise without decreasing resolution.

SUMMARY OF THE INVENTION

One aspect of the invention is a radiation detector comprising a luminescence means for producing light in response to incident radiation and photoelectric means optically coupled with the luminescence means for producing electrical signals in response to light received from the luminescence means. The luminescence means has at least a first dimension comprised of at least a first segment and a second segment. The first and second segments of the luminescence means receive radiation and produce light. The output signal of the photoelectric means is more responsive to the light produced in response to radiation received by the first segment than to the light produced in response to radiation received by the second segment. As a result, variations in the amount of radiation received adjacent the first segment will cause greater variations in the electrical signals than variations in the intensity of radiation received adjacent the second segment.

Another aspect of the invention is a radiation detector comprising a first scintillation crystal, a second scintillation crystal, and a photoelectric means optically coupled with the first and second scintillation crystals.

Another aspect of the present invention is a computerized tomographic scanning apparatus for examining a planar slice of an object in the plane of a scan circle with radiation and producing a representation of an image of the planar slice. The apparatus comprises a radiation source for producing at least one beam of radiation in the plane of the scan circle; a radiation detector means which has a non-constant spatial response along a first dimension in the plane of the beam for producing electrical signals in response to radiation received from the source that has traversed the scan circle; and a processing means for processing the electrical signals to produce the representation of an image.

BRIEF DESCRIPTION OF THE DRAWINGS

The invention may take physical form in certain parts and arrangements of parts, preferred and alternate embodiments of which will be described in detail in this specification and illustrated in the accompanying drawings which form a part hereof.

FIG. 1 illustrates a tomographic scanner in accordance with the present invention;

FIG. 2A illustrates a radiation detector in accordance with the present invention;

FIGS. 2B and 2C illustrate spatial responses of detectors in accordance with the present invention;

FIG. 3 illustrates modulation transfer functions associated with the responses of FIGS. 2B and 2C;

FIG. 4 illustrates a preferred embodiment of a radiation detector in accordance with the present invention;

FIG. 5A illustrates a side section of an alternate embodiment of a radiation detector in accordance with the present invention;

FIG. 5B shows a preferred top section through section 5—5 of FIG. 5A;

FIG. 5C shows an alternate top section through sections 5—5 of FIG. 5A;

FIG. 6 illustrates a side section of an alternate embodiment of a radiation detector in accordance with the present invention;

FIG. 8 illustrates a side section of another embodiment of a radiation detector in accordance with the present invention;

FIG. 9 illustrates another alternate embodiment of a radiation detector in accordance with the present invention;

FIG. 10 illustrates another alternate embodiment of a radiation detector in accordance with the present invention;

DESCRIPTION OF THE PREFERRED EMBODIMENT

Figure 4A:
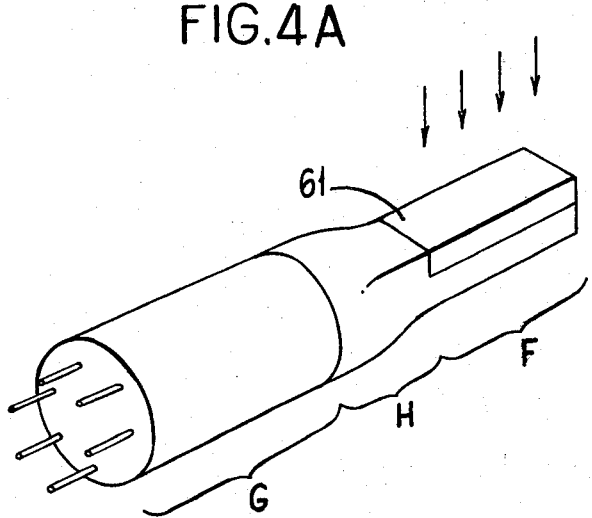
FIG. 4A illustrates a preferred embodiment of a single crystal radiation detector in accordance with the present invention.

Referring now to the drawings, the drawings are for the purpose of illustrating preferred embodiments of the invention only, and not for purposes of limiting the invention. The figures, note FIG. 1, show a computerized tomographic scanning apparatus A. A rotating fan beam type scanner is illustrated; however, the invention is also applicable to traverse and rotate, and other types of scanners. The scanner includes a scan circle B which is adapted to receive a planar region of a patient to be examined. Adjacent the scan circle, is a rotatably mounted source of radiation C for irradiating the scan circle with a generally planar fan array of beams of radiation. Disposed opposite the scan circle from the source of radiation is a radiation detector means D. The radiation detector means has a non-constant or varying spatial response along a first dimension or width. The non-constant spatial response causes the detector means to weight the intensity of radiation received along a first more responsive segment of its width more heavily than radiation received along other less responsive segments. The detector means produces electrical signals indicative of the weighted sum or average of the amount of radiation received. As the source rotates, the radiation received by a detector traverses successive paths through the patient. The intensity of the radiation received varies with the coefficient of absorption of material along each path. This causes variations in the electrical signal. The variations in the amount of radiation received along the first, more heavily weighted segment of the width cause a correspondingly greater variation in the electrical signal than variations in the intensity of radiation received along less heavily weighted segments. A processing means E operates on the signals with algorithms well known in the tomographic art to produce a representation of the image of the planar region of the patient being examined.

In the preferred embodiment the detector means comprises a plurality of radiation detectors which have a non-constant spatial response along the first dimension or width. Each of the radiation detectors, note for example FIG. 2A, comprises a luminescence means F for transforming or converting variations in incident radiation intensity into variations in light intensity. Optically coupled with luminescence means F is a photoelectric means G for receiving light from the luminescence means F and producing variations in an electrical signal in response to variations in the intensity of the received light. The detectors may further include an optical coupling means H for transmitting light from the luminescence means to the photoelectric means.

The present invention contemplates several embodiments in which one or more of the luminescence means F, photoelectric means G or optical coupling means H are designed to achieve the non-constant spatial response of the detector. Causing a non-constant response by partially blocking radiation from reaching the detector is undesirable because a patient is subject to radiation which is not used to produce the tomographic image. Rather than blocking radiation, the detector means or the detectors themselves produce a non-constant response. The beam of radiation from the source to a detector can be described in cross-section in terms of its thickness and its width. The spatial response of the detector of the present invention is described below in one dimension in terms of the response across the width of the detector. It will be appreciated that two and three dimensional non-constant spatial responses of the detectors are also included within the present invention as well as non-constant spatial responses in other directions, non-constant energy responses, and the like.

FIGS. 2B and 2C provide a graphic comparison of the spatial response of conventional detectors, curve 10, and the spatial response of detectors in accordance with the present invention, curves 12, 14, 16 and 18. The vertical axis of FIGS. 2B and 2C represents the magnitude of the response and the horizontal axis represents the spatial position along the width of the detector.

Response 10 may be described mathematically as:

$$f(x) = 1 \quad -A \leq x \leq A \quad (1)$$
$$= 0 \quad |x| > A$$

The spatial frequency response of the detector can be described in terms of a modulation transfer function (MTF). The modulation transfer function may be determined mathematically from the Fourier transform of the response. The modulation transfer function of response 10 described by equation (1) is expressed as:

$$g(k) = 2 \int_0^A \cos(2\pi k x) dx = \frac{\sin(2A\pi k)}{\pi k} \quad (2)$$

The normalized modulation transfer function, which approaches unity as k becomes very small, is:

$$g_n(k) = \frac{\sin(2A\pi k)}{2A\pi k} \quad (3)$$

The modulation transfer function g(k) has zero amplitude at certain spatial frequencies. The first zero occurs at the spatial frequency $k_{01}$ which is found as follows:

$$g(k_{01}) = 0 = \sin(2A\pi k) = \sin(\pi). \tag{4}$$

Thus, the first zero of the spatial frequency $k_{01}$ is:

$$k_{01} = \tfrac{1}{2}A. \tag{5}$$

The modulation transfer function of response 10 is illustrated by curve 10' of FIG. 3. The first zero, 20, in the spatial frequency is $\tfrac{1}{2}A$ units from the coordinate axis.

By appropriately constructing the luminescence means, optical coupling means, and photoelectric means, other spatial responses, as shown by curves 12, 14, 16 and 18, can be achieved. The generally triangular response, curve 12, can be expressed:

$$\begin{aligned} f(x) &= 1 - |x| & -A \leq x \leq A \\ &= 0 & |x| > A \end{aligned} \tag{6}$$

The normalized modulation transfer function of this curve can be shown to be:

$$g_n(k) = \left[\frac{\sin(A\pi k)}{A\pi k}\right]^2 \tag{7}$$

The first zero of the spatial frequency is:

$$K_{01} = 1/A. \tag{8}$$

By comparing equations (5) and (8) above, it can be seen that the spatial frequency of the first zero for a generally triangular detector response is double the spatial frequency of a generally rectangular response. The modulation transfer function of curve 12 is illustrated graphically as curve 12' of FIG. 3. The first zero 22 of the spatial frequency of curve 12' is shown 1/A units from the coordinate axis. Doubling the spatial frequency halves the size element which may be resolved, i.e., doubles the resolution. Yet the size of the aperture, hence, the number of x-ray photons received, remains the same. Thus, the noise level remains substantially the same while the resolution is substantially doubled.

Further, for some applications it may be desirable to weight two or more separated areas of the beam more heavily. For example, the spatial response may be described as a generally bell-shaped curve with a dimple at the apex. Yet, other spatial responses such as a truncated triangular wave, curves 16 or 18, or the like may be employed. This small alteration in the wave form may provide improved edge enhancement or other benefits in the reconstructed image.

Other spatial distributions can be used to weight part of the beam more heavily. Curve 14 illustrates a bell-shaped spatial response which by similar analyses can be shown to have a spatial frequency of 1/A. An advantage of a generally bell-shaped spatial response is that the modulation transfer function is also a bell-shaped distribution as shown by curve 14 in FIG. 2B. The bell-shaped modulation transfer function 14' approaches the first zero of the spatial frequency 1/A asymptotically, whereas modulation transfer functions 10' and 12' are generally sinusoidally damped.

The photoelectric means, such as photomultiplier tubes, photodiodes, or the like, produces an electrical signal whose amplitude is proportional to the amount of light received from the luminescence means. Variations in the intensity of the light produce corresponding variations in the amplitude of the electric signal. The area of the luminescence means at the first, more responsive segment of the detector width, produces a greater intensity of light from a given number of radiation photons than do adjacent less responsive segments. For the responses illustrated in curves 12, 14, 16 and 18, the first, more responsive segment is centrally located relative to the width and the less sensitive areas are peripherally located relative to the width.

In examining a planar slice, the beam of radiation has a finite width. A relatively dense incremental element which is small in comparison to the width of the beam will cast a shadow on part of the detector when it is in the path of the beam. More accurately, the incremental element absorbs some photons of the radiation producing a shadow of a reduced number of photons. If the shadow is cast on the central, more responsive segment of the detector width, a relatively large reduction in the amplitude of the electrical signal results. If the shadow is cast on the peripheral, less responsive segment, a relatively small reduction in the amplitude of the electrical signal results. In this manner, variations in the electrical signal are affected more greatly by incremental elements in the central part of the beam than by incremental elements in a peripheral part of the beam. Thus, the detector weights the response in favor of radiation impinging on the more responsive segments of its width.

The invention may be implemented with numerous physical embodiments. FIG. 1 illustrates a computerized tomographic scanner A with radiation detectors in accordance with the present invention. A rotating fan-beam type scanner is illustrated; however, it should be appreciated that the present invention is equally applicable to traverse and rotate, and other types of scanners.

The scanner comprises a tubular element 30 which functions to support a patient 32 or other object to be examined. The source of radiation C is mounted for rotational movement about element 30. The source comprises x-ray tube 34 and a shutter mechanism 36 for defining a continuous swath of radiation diverging from substantially a point source. The shutter mechanism may be adjustable for selecting different size scan circles and different thicknesses of patient slices for examination. Alternately, the shutter mechanism may divide the radiation swath into a plurality of narrow, discrete beams. A reference detector 38 measures the intensity of the radiation before it traverses the scan circle. A means 40 rotates the source of radiation and provides an indication of the angular orientation of the source relative to the scan circle.

The radiation detector means D may take several forms as illustrated below. The detector means may comprise an arc of detectors which rotates with the source of radiation. The arc is defined by the maximum fan beam of radiation. The detector means may comprise an arc of stationarily mounted detectors. The stationary detectors may span an arc 42-44 defined in phantom or may circumscribe the scan circle. A support structure with small flanges such as 46 slightly overlaying the responsive surface of the detectors holds the detectors in place. The spacing between adjacent flanges determines the beam width. An exemplary beam 48 in the continuous fan-shaped swath of radiation has a width 50.

The detector means D and reference detector 38 are connected to a comparator 52 of processing means E. The comparator 52 compares the intensity of radiation before and after traversing the scan circle. The comparator provides a processor 54 with a series of indications of the logarithm of the radiation attenuation along various paths through the scan circle. Processor 54 operates on the data with conventional algorithms to produce an electronic representation of the tomographic image for display on video monitor 56. A suitable processor is described in co-pending application Ser. No. 838,084 filed Sept. 30, 1977 and now abandoned, the disclosure of which is incorporated herein by reference.

A preferred embodiment of a detector from detector means D is illustrated in FIG. 4. The detector comprises luminescence means F and photoelectric means G which are optically coupled by coupling means H. The luminescence means comprises a first or central scintillation crystal means 60, such as a crystal of cadmium tungstate or calcium tungstate. The central scintillation crystal means has a configuration of a solid figure, preferably a rectangular prism. The solid figure has two oppositely disposed planar faces. A second scintillation crystal means comprises a pair of crystals 62 and 64 oppositely disposed adjacent the central scintillation. Crystals 62 and 64 have the configurations of solid figures, each having a generally planar face disposed adjacent to and parallel with one of the generally planar faces of central scintillation crystal means. In the preferred embodiment, these solid figures are also rectangular prisms. The pair of scintillation crystals 62 and 64 may be bismuth germanate (BGO). The generally planar faces of the rectangular prisms are oriented generally perpendicular to the width of first dimension and generally parallel to the received radiation. This provides a non-constant spatial response across the planar faces along the width.

Cadmium tungstate produces essentially the same number of scintillations as BGO from a given number of photons of x-rays. However, the cadmium tungstate scintillations are brighter than the BGO scintillations. Thus, the cadmium tungstate generates a greater intensity of light than BGO from the same number of photons of incident radiation. The spatial response of the detector is describable by curve 18 of FIG. 2C. BGO generates blue light and cadmium tungstate generates a yellow-orange light. Silicon photodiodes are generally more sensitive to light in red range than to blue light. Thus, the light from cadmium tungstate has the effect of light with a greater intensity than a like intensity of blue light. Photomultiplier tubes on the other hand, are generally more sensitive to light in the blue range. Various combinations of crystals may be selected. The crystal to be placed adjacent the segment(s) of the width to be weighted most heavily should have the higher conversion efficiency or best match to the spectrum of the photoelectric means. Table 1 provides a list of some suitable crystals with the peak emission and conversion efficiency characteristics.

| MATERIAL | WAVELENGTH OF MAXIMUM EMISSION (nm) | SCINTILLATION CONVERSION EFFICIENCY* |
|---|---|---|
| NaI(Tl) | 410 | 100 |
| CaF$_2$(Eu) | 435 | 50 |
| CsI(Na) | 420 | 85 |
| LiI(Eu) | 470–485 | 35 |
| TlCl(BeI) | 465 | 2.5 |
| CsF | 390 | 5 |
| BaF$_2$ | 325 | 10 |
| Bi$_4$Ge$_3$O$_{12}$ | 480 | 8 |
| KI(Tl) | 426 | 24 |
| CaWO$_4$ | 430 | 50 |
| CdWO$_4$ | 530 | 65 |
| CsI(Tl) | 560 | 4.5 |

*As a percent of the conversion efficiency of NaI(Tl)

Alternately, the luminescene means F may be a doped scintillation crystal, such as NaI(Tl) or CsI(Tl) with a spatially variant density of doping material along its width such as by ion implanting.

By varying the density of the dopant, thallium, i.e., the activator in the crystal, along the width of the scintillation crystal, the desired non-constant spatial response is accomplished in a single crystal 61, as shown in FIG. 4A. This embodiment obviates the need to size, align and join several pieces of crystals of at least two different types in a composite assembly of the type shown in FIG. 4.

In computerized tomographic scanning systems of the type having several hundred or even thousands of detectors, each detector is necessarily quite narrow, on the order of a few millimeters. This alternative provides a significant advantage of ease of assembly since each of these detectors would otherwise require the glueing together of three crystal solids in sandwich fashion to achieve the desired shaped response. The variant density of the activator is distributed in the crystal along one dimension thereof to produce an x-ray conversion efficiency gradient.

The desired distribution of the activator is accomplished in one of two ways depending on whether or not the starting material has an activator. For crystals such as NaI or CsI having an activator, typically thallium, the gradient is induced by expelling a portion of the activator. This is achieved by heating the crystal. The application of heat over a specified period of time forces an outward migration of the activator from the crystal slab, leaving the central region with a greater density of the dopant than at either edge. Thus, the crystal's response will be positionally dependent. The response can be shaped as desired by the controlled application of time and temperature in the processing of the crystal slab.

The following examples are illustrative of the curing process of a slab of CsI(Tl):

EXAMPLE 1

The crystal was heated for one hour at 525° C. No change in output response was noted.

EXAMPLE 2

The crystal was heated for 17 hours at 530° C. The change in output response was minimal.

EXAMPLE 3

The crystal was heated for 18½ hours at 575° C. This showed a distinct shaping of the output response similar to the bell-shaped distribution shown by curve 14 in FIG. 2B.

EXAMPLE 4

The crystal was heated for 21 hours at 550° C. The results are similar to that found in Example 3.

Figure 13A:
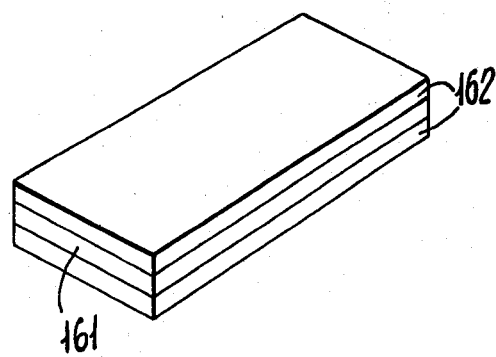
FIG. 13A illustrates a slab of a scintillation crystal.
Figure 13B:
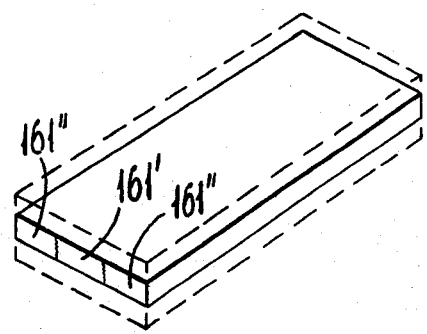
FIG. 13B illustrates the slab of crystal of FIG. 13A after the slab has been treated in preparation for use in the detector shown in FIG. 4A.

In both of the successful results, i.e., Examples 3 and 4, there was a significant drop in light output of about 50%. However, the desired shaped response was achieved without a noticeable light output loss by shearing off the top and bottom faces 162 of the cured crystal slab. FIGS. 13A and 13B illustrate diagrammatically a slab of cured crystal before and after the top and bottom faces 162 are sheared off. FIG. 13B illustrates the "core" crystal 161, after the shearing step. The core crystal has a high conversion efficiency region 161' and lesser conversion efficiency regions 161" analogous, respectively, to crystal 60 and crystals 62, 64 in the embodiment discussed in connection with FIG. 4. This core 161 is ready for cutting into the desired thickness such as for example, 3 mm, for individual detector size.

Alternatively, the crystal initially may be devoid of an activator. This would be the situation when a crystal with a relatively high luminescence or high conversion efficiency is used such as, for example, cadmium tungstate, $CdWO_4$. Because of their naturally high luminescence, such crystals need no activators to perform well as scintillation detectors in CT scanners. In order to obtain the desired non-constant spatial response in a non-doped crystal, an impurity must be induced into the crystal such as by diffusion. For example, the crystal is placed into a vacuum chamber filled with an impurity. When the chamber is heated, the impurity will diffuse into the crystal, in effect, poisoning it. The degree of desired contamination by the impurity is achieved by controlling the time and temperature of the process to yield the desired gradient of impurity in the crystal along at least its width. Since the impurity has to enter the crystal from the surrounding atmosphere, the concentration of the impurity will, at least initially, be greater at peripheral portions of the crystal than in its central portion. And since the introduction of the impurity lessens the conversion efficiency of the crystal in relation to its concentration in the crystal, an uneven distribution of the impurity will allow the crystal and hence the detector to exhibit a non-constant spatial response.

The optical coupling means H is a section of LU-CITE shaped at one end to match the luminescence means and shaped at the other to match the light sensitive area of the photoelectric means. The photoelectric means G may be a photomultiplier tube such as a Hamatsu photomultiplier tube Model No. R-647. Alternately, the photoelectric means may be a photodiode, as illustrated in U.S. Pat. No. 4,070,581, issued Jan. 24, 1978.

FIGS. 5A, 5B and 5C show an alternate embodiment of a radiation detector in which the luminescence means produces the non-constant spatial response of the detector. Like elements in FIGS. 5A, B and C are marked with the same reference numeral as corresponding elements in FIG. 4 followed by a prime ('). Radiation impinges on a top face 66 of the luminescence means. The luminescence means comprises a central scintillation crystal means 60' surrounded by a second scintillation crystal means 62' adjacent the first more responsive segment of the detector width. As shown in FIG. 5B, the central scintillation crystal means may have the configuration of a solid figure with a convex arcuate face such as a cylinder. The second scintillation crystal means may have a configuration of a solid figure with a concave arcuate face disposed adjacent the convex arcuate face such as a surrounding tube. Unlike the embodiment of FIG. 4 which had a non-constant spatial response in only one dimension, the embodiment of FIG. 5B has the same non-constant spatial response in two dimensions. The embodiment of FIG. 5B is ideally suited for x-y flaw detectors and patterns. Alternately, as shown in FIG. 5C, the central scintillation crystal means may be a generally rectangular prism and the second scintillation means a generally rectangular surrounding tube. This provides improved resolution in the width and thickness dimensions for radiation beams of the thickness of the full crystal thickness. However, beams of a lesser thickness have improved resolution only in the width dimension.

A radiation permeable but light impermeable coating 68, such as black plastic or paint encases the luminescence means and the optical coupling means to prevent stray light from causing false signals. Optical coupling means H may be a conventional optical coupling cement.

FIG. 6 shows another alternate embodiment of a radiation detector in which the luminescence means produces the non-constant spatial response of detector. Like elements in FIG. 6 are marked with the same reference numerals as corresponding elements in FIGS. 4 and 5 followed by a double prime ("). Radiation impinges along the width of top face 66". The luminescence means comprises a scintillation crystal means 70. Preferably, the scintillation crystal is a single crystal of BGO, although means 70 may be other scintillation crystals. The luminescence means further comprises a covering means having a first part 72 and a second part 74. The first part has a light reflective surface disposed at the segment of detector width that is to be weighted more heavily. The second part 74 has a less reflective surface disposed adjacent the part or parts of the scintillation crystal means that are at segments of the width to be weighted less heavily. The first part is a thin polished metallic foil and the second part is black paint. A coating 68" may encase the covering means.

Figure 7:
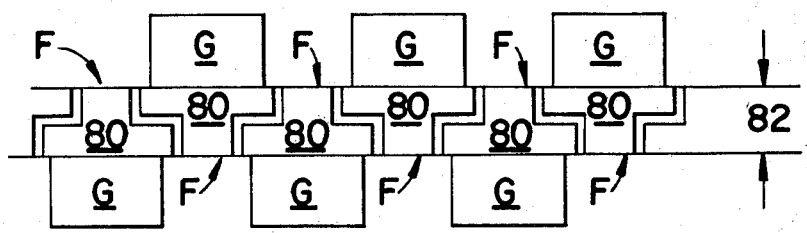
FIG. 7 illustrates a top plan view of a linear array of radiation detectors in accordance with the present invention.

FIG. 7 illustrates a top view from the perspective of the radiation source of yet another embodiment of a radiation detector in which the luminescence means produces the non-constant spatial response of the detector. The luminescence means F has a non-constant cross-section transverse to the beam which roughly corresponds to the non-constant spatial response of the detector. The luminescence means comprises a scintillation crystal means having the configuration of a solid figure. The solid figure has a generally planar top surface 80 and a generally planar bottom surface disposed generally parallel to the top surface; the top and bottom surfaces having generally T-shaped profiles. The top surface spans the width of the detector and the maximum thickness of the x-ray beam. The greater amount of crystal adjacent the central section of the photoelectric means G and the lesser amount of crystal adjacent the periphery of the width causes a non-linear spatial response weighted more heavily toward the center. Each T-shaped face is oppositely disposed from the T-shaped face of the adjacent detectors. The T-shaped detectors mesh to form a linear array. Adjacent crystals are optically isolated. Further, the symmetry relative to the thickness dimension 82 allows the shutter 36 to contract the beam thickness without altering spatial response. Alternately, the luminescence means may have other cross-sections such as triangular, sinusoidal, or various other meshing or interlocking configurations. Further, the luminescence means may comprise a scintillation means comprising a plurality of optically coupled crystals.

FIG. 8 shows another embodiment in which the luminescence means produces the non-constant spatial response of the detector. Like elements in FIG. 8 are marked with the same reference numerals as FIGS. 4 through 6, followed by a triple prime ('''). The luminescence means comprises first and second scintillation crystal means. The second scintillation crystal means comprises a BGO scintillation crystal 62''' having a slot cut transverse to its width. Crystal 62''' is relatively thick adjacent the less responsive segments of the detector width and has relatively thin bridge 90 adjacent the more responsive segment of the detector width. The first scintillation crystal means comprises a cadmium tungstate scintillation crystal 60''' disposed in the slot of crystal 62'''.

Crystal 60''' and bridge 90 of crystal 62''' are disposed adjacent the first more sensitive segment of the detector width.

There is a tendency for x-rays of a higher energy to penetrate deeper into a scintillation crystal before producing a scintillation than x-rays of a lower energy. Accordingly, the scintillations produced in crystal 60''' are produced primarily in response to relatively low energy photons and the scintillations in bridge 90 are produced in response to relatively high energy photons. This non-constant responsiveness along the path of the radiation beam produces a non-constant energy or spectral response of the detector. Particularly, lower energy x-ray photons tend to produce a higher intensity of light than high energy x-ray photons.

The division between higher and lower energy x-ray photons is selected by selecting the dimension of crystal 60''' in the direction of x-ray travel. The non-constant spectral response can also be created adjacent the less responsive segments of the detector. A suitable construction is six crystals stacked two deep across the width of the detector. By selecting crystals with two or three conversion efficiencies and by selecting the depth of each crystal, various non-constant spatial and spectral responses can be achieved. If the higher energy photons are to be weighted more heavily, the crystal with the lower conversion efficiency is placed on the top and the crystal with the higher conversion efficiency on the bottom. To emphasize a middle energy range, a sandwich of three or more crystals may be employed. The invention further includes detectors with a constant spatial and non-constant spectral response.

Alternatively, the optical coupling means can be constructed to produce the non-constant spatial response of the detector. FIG. 2A illustrates such an embodiment. A scintillation crystal means 100, such as a single crystal of BGO, receives incident radiation and generates light of a constant intensity across the width of the detector. A coating means 102 such as metallic foil prevents stray light from causing false signals and reflects light back into crystal 100 to increase the intensity. The optical coupling means H comprises a filter means 104. The filter transmits a greater intensity of the light produced in response to radiation received at the segment of the width to be weighted most heavily. The filter means may vary in opacity, index of refraction, color, reflectivity or the like. An optical coupling grease may be employed to couple the filter means with the luminescence means and the photoelectric means. Alternately, the optical coupling means may comprise diverging and converging light pipe to redistribute the light from the luminescence means.

Alternatively, the photoelectric means can be constructed to produce the non-constant spatial detector response to the detector. FIG. 9 illustrates such a embodiment. The luminescence means F comprises a first scintillation crystal means 110. The first crystal means comprises three laminar crystals. The luminescence means further comprises second scintillation crystal means 112 and 114 adjacent the first scintillation crystal means. The photoelectric means comprises a first photoelectric transducer means 116 adjacent the first scintillation crystal means and second photoelectric transducer means 118 and 120 adjacent the second scintillation crystal means 112 and 114, respectively. The first scintillation crystal means generates a greater intensity of light than the second scintillation crystal means. Alternatively, the luminescence means may be a single crystal and the first photoelectric transduer means may be more sensitive to the light generated than the second photoelectric means. In the preferred embodiment, the first and second photoelectric transducer means are photodiodes. The photodiode 116 adjacent the first scintillation crystal means is connected to one input of a differential amplifier 122. Photodiodes 118 and 120 disposed adjacent the second scintillation crystal means are connected with a second input of the differential amplifier. This produces a response as illustrated by curve 16 of FIG. 2C.

Alternatively, scintillation crystal 112 and photodiode 118 may be replaced with a first solid state or ionization detector; scintillation crystals 110 and photodiode 116 may be replaced with a second solid state or ionization detector; and scintillation crystal 114 and photodiode 120 may be replaced with a third solid state or ionization detector. One of the solid state or ionization detectors, e.g., the center detector, may be selected to have a greater sensitivity to the incident radiation than the other two.

FIG. 10 shows another alternate embodiment in which the photoelectric means produces the non-constant spatial response. Like elements in FIG. 10 are marked with the same reference numerals as FIG. 9 followed by a prime ('). The luminescence means F comprises first scintillation crystal means 110' and second scintillation crystal means comprising crystals 112' and 114', flanking the first scintillation crystal means. The photoelectric means comprises a first photoelectric transducer means 116' adjacent the first scintillation crystal means and second photoelectric transducer means comprising transducers 118' and 120' adjacent crystals 112' and 114' respectively.

Connected with photoelectric means is a means 124 for determining the rate of change of the intensity of radiation received by the detector. In the preferred embodiment, this rate of change means comprises a comparator for comparing the amount of radiation received by crystals 112' and 114'. As the radiation path moves relative to the patient, the radiation impinging on crystals 112' and 114' is substantially the same when the rate of change is low. But when the radiation path moves through parts of the patient which cause sudden changes in the intensity of radiation passing through the patient the outputs of transducers 118' and 120' become unbalanced. When comparator 124 detects a state of unbalance, it causes the input of differential amplifier 122' from transducers 118' and 120' to be reduced by attenuator means 125. Means 125 may be a variable resistor, or the like, which attenuates the signals from transducers 118' and 120' to a greater or lesser degree as the comparator 124 becomes more or less unbalanced respectively. Attenuating means 125 may alternately be a switch which totally cuts off the signals from transducers 118' and 120' when the comparator becomes unbalanced. In this manner, the effective size of the detector is decreased when the radiation intensity traversing the patient varies rapidly with spatial movement of the radiation path and is increased when the radiation intensity varies slowly.

Figure 11:
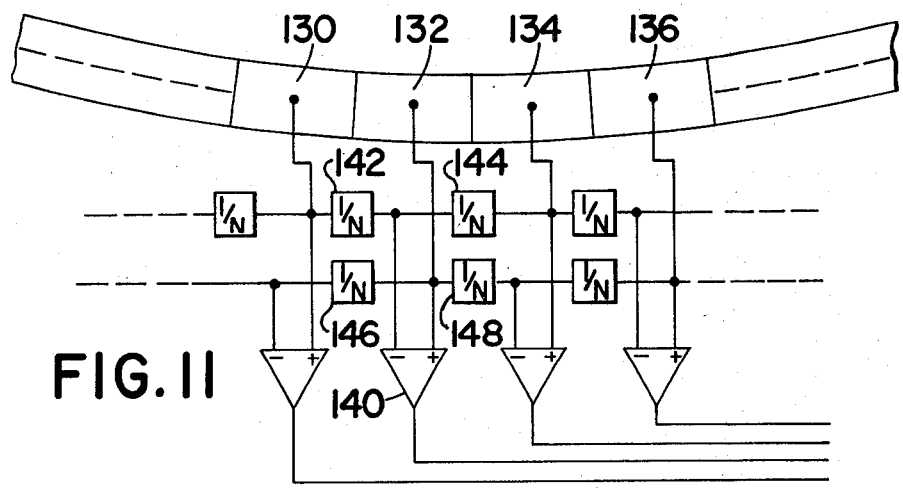
FIG. 11 illustrates an alternate embodiment of detector means in accordance with the present invention.

FIG. 11 illustrates another detector means having a non-constant spatial response. The detector means comprises a plurality of detectors such as ionization chambers and an electronic means for altering the signals of each of the detectors with the electrical signals from at least one other detector. Four of the detectors 130, 132, 134 and 136 are illustrated. Detector 132, for example, is connected with one input of a combining means 140. Another input of the combining means is connected with means 142 for altering the amplitude of the electrical signal from adjacent detector 130 and with means 144 for altering the amplitude of the electrical signal from detector 134. Means 142 and 144 in the preferred embodiment are means for reducing the amplitudes, such as a series connected resistor and diode. Detector 132 is also connected with means 146 and 148 for reducing the amplitude of the electrical signals from detector 132 and supplying the reduced signals to combining means associated with detectors 130 and 134. In the preferred embodiment, the combining means are differential amplifiers for subtractively combining each signal with the reduced signals. Rather than reducing the amplitude of the electrical signals from the adjoining detectors, the signal from each detector can be increased and combined with the signals from adjoining detectors. The combining means and altering means comprise the electronic means for altering the signals. The detectors may also be solid state detectors, scintillation crystal-photoelectric detectors, one of the preceding detectors, or the like.

Figure 12:
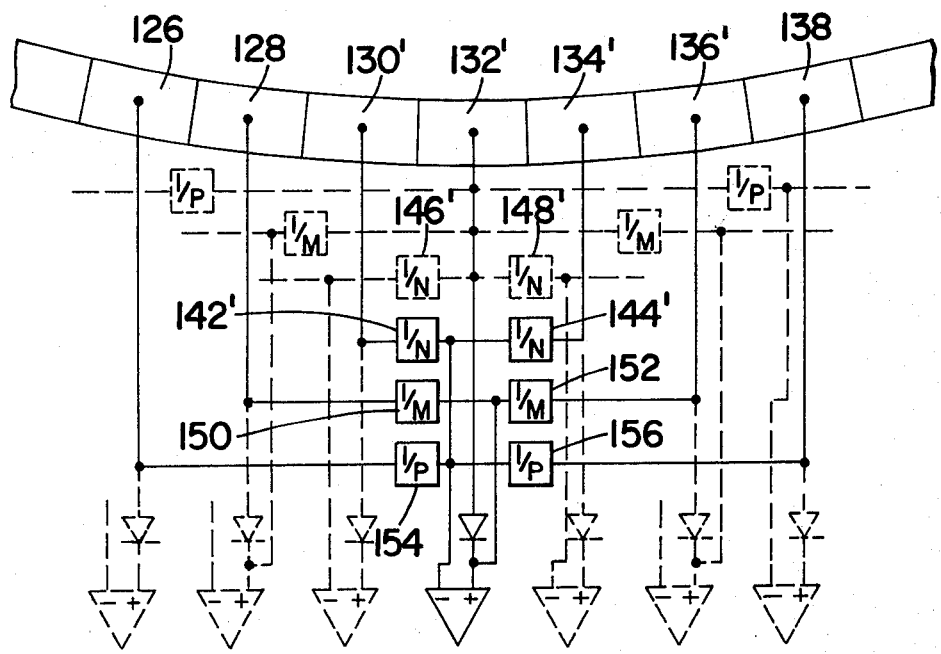
FIG. 12 illustrates an alternate embodiment of the detector means of FIG. 11.

FIG. 12 is an alternate embodiment of the detector means of FIG. 11. Like elements in FIG. 12 are marked with the same reference numerals as corresponding elements in FIG. 11 followed by a prime ('). The detector means comprises a plurality of adjacent detectors connected with a convolution means. The convolution means is analogous to the electronic altering means of FIG. 10 except that it alters the signals from each detector with the signals from an arc segment of detectors. The number of detectors which contribute to the alteration is determined by the convolution function chosen. A common convolution function subtracts a fraction of the adjoining detectors signal, adds a smaller fraction of the next adjoining detectors, subtracts a still smaller fraction of the next closest detectors, etc. FIG. 11 illustrates this convolution function, but other functions, such as those which skip some closer detectors and add or subtract components of some further detectors, may be similarly implemented. For simplicity of illustration, only the components which are combined with the electrical signal of detector 132 are illustrated. The components which contribute fractional parts of the signal from detector 132 to adjust other detector signals are shown in phantom. Altering means 142' and 144' reduce the electric signals from detectors 130' and 134' and supply them to the inverting input of a combining means 140'. Altering means 150 and 152 reduce the electric signals from detectors 128 and 136'. The reduced signals from reducing means 150 and 152 are supplied to the non-inverting input of combining means 140'. Altering means 154 and 156 reduce the electric signals from detectors 126 and 128 and supply the reduced signals to the inverting input of combining means 140'. Further, altering means may contribute fractional parts of the electric signals from other detectors. In the preferred embodiment, altering means 154 and 156 reduce the signal more than altering means 150 and 152 which in turn reduce the signals more than altering means 142' and 144'. The detectors may be ionization chambers, solid state detectors, scintillation crystal-photodiode or photomultiplier tube detectors, one of the detectors of FIGS. 2-9, or the like.

The invention has been described with reference to prefered and alternate embodiments. Obviously, modifications and alterations will occur to others upon reading and understanding this specification. The features of several embodiments may be combined in full or in part. Such combinations may produce more smoothly varying or more elaborate non-constant spatial or spectral responses or combinations of one or two dimensional spatial and spectral responses. It is my intention to include all such modifications, alterations and combinations insofar as they come within the scope of the appended claims or their equivalents.

I claim:

1. A computerized tomographic scanning apparatus for examining with radiation a planar slice of an object in the plane of a scan circle and producing a representation of an image of the planar slice, comprising:
   at least one source of radiation for producing at least a beam of radiation in the plane of said scan circle;
   radiation detector means having at least one radiation detector for producing electrical signals in response to received radiation, said detector means disposed to receive from the source radiation which has traversed the scan circle, said radiation detector including a scintillation crystal for converting variations in incident radiation intensity into variations in light intensity, said scintillation crystal having a spatially variant radiation conversion efficiency such that said radiation detector has a non-constant spatial response in at least a first dimension in the plane of the scan circle; and
   processing means for processing the electrical signals from the detector means to produce the representation of an image.

2. A computerized tomographic scanning apparatus according to claim 1 wherein said scintillation crystal is doped with an activator.

3. A computerized tomographic apparatus according to claim 2 wherein the density of said activator in said scintillation crystal is distributed therein such that the detector is more responsive to radiation toward the center of said first dimension then toward either edge thereof.

4. A computerized apparatus according to claim 1 wherein the response of said detector is characterized by a generally bell shaped function.

5. A computerized tomographic apparatus according to claim 2 wherein the scintillation crystal is sodium iodide.

6. A computerized apparatus according to claim 2 wherein the scintillation crystal is cesium iodide.

7. A computerized tomographic apparatus according to either of claims 5 or 6 wherein the activator is thallium.

8. A computerized tomographic apparatus according to claim 1 wherein said scintillation crystal has a relatively high scintillation conversion efficiency such as cadmium tungstate, wherein said crystal has an impurity distributed therein in a gradient along said first dimension.

9. An apparatus according to claim 1 wherein said scintillation crystal is more responsive to radiation received along a first centrally disposed portion of the crystal than to radiation received along at least a second peripherally disposed portion of the crystal, said second portion disposed adjacent the first portion along the first dimension, whereby the crystal weights radiation received adjacent the center of the detector more heavily than radiation received adjacent the edges.

* * * * *